United States Patent [19]

Simionescu

[11] 4,111,228
[45] Sep. 5, 1978

[54] RESPIRATORY VALVE, ESPECIALLY FOR ANAESTHETIC CIRCUITS

[75] Inventor: Radu Simionescu, Bucharest, Rumania

[73] Assignee: Institutul Oncologic Bucuresti, Bucharest, Romania

[21] Appl. No.: 754,992

[22] Filed: Dec. 28, 1976

Related U.S. Application Data

[63] Continuation-in-part of Ser. No. 598,360, Jul. 23, 1975, abandoned.

[51] Int. Cl.$^2$ ............................................. F16K 15/14
[52] U.S. Cl. ............................. 137/512; 137/512.15; 137/855
[58] Field of Search .................... 137/512, 512.15, 102, 137/855; 128/185, 210, 211, 203, 207

[56] References Cited

U.S. PATENT DOCUMENTS

| | | | |
|---|---|---|---|
| 2,104,988 | 1/1938 | Heidbrink | 128/203 |
| 2,121,196 | 6/1938 | Heidbrink | 128/203 X |
| 2,228,983 | 1/1941 | Bloomheart | 128/203 X |
| 3,028,873 | 4/1962 | Kindred | 137/512 |
| 3,568,977 | 3/1971 | Nelson | 137/855 X |
| 3,643,686 | 2/1972 | Koegel | 137/512 |
| 3,812,878 | 5/1974 | Bird et al. | 137/512 |
| 3,902,516 | 9/1975 | Rudolph | 137/512 X |

*Primary Examiner*—William R. Cline
*Attorney, Agent, or Firm*—Karl F. Ross

[57] ABSTRACT

A respiratory valve, especially for use in the circuits of anaesthetic gas devices, having a body member formed with two arms in a V configuration, intended for inhalation and exhalation, respectively, and a tubular mouthpiece fitting. To the two arms are connected, by joints, an inhalation fitting and an exhalation fitting, respectively; the joints retain each the fastening ring of a shutter, the resilient membrane of which closes and opens in response to the gas circulation, as required.

4 Claims, 3 Drawing Figures

U.S. Patent  Sept. 5, 1978  4,111,228
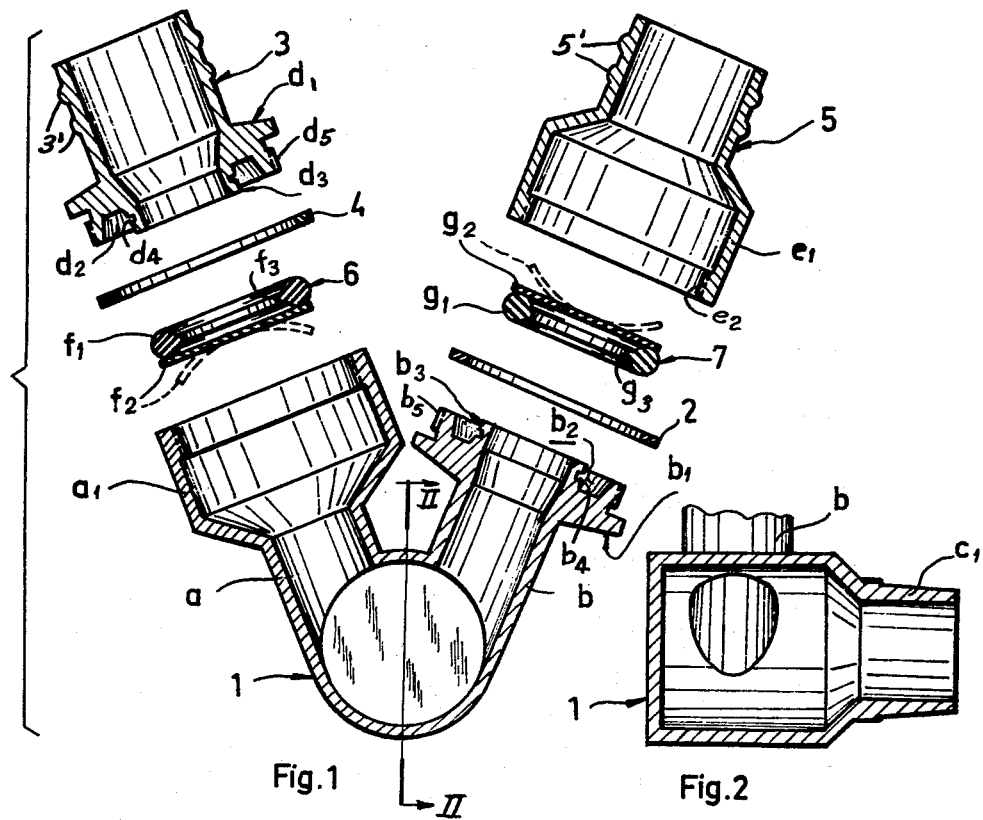
Fig.1
Fig.2
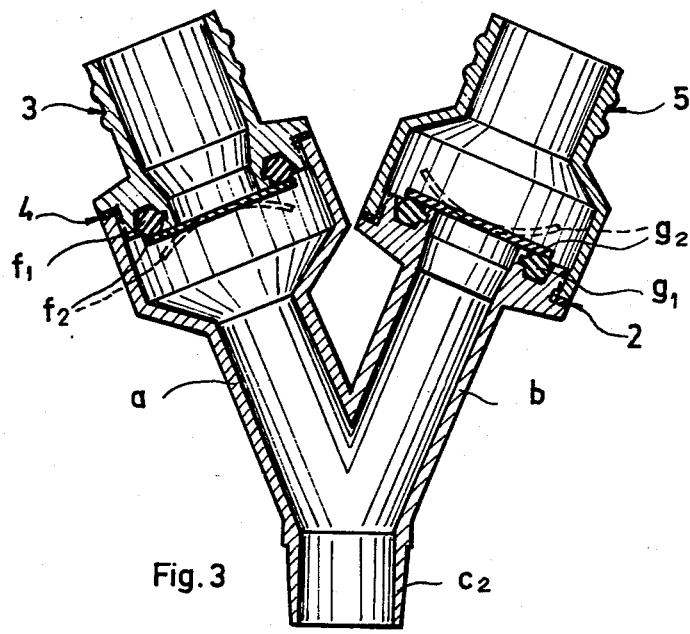
Fig.3

RESPIRATORY VALVE, ESPECIALLY FOR ANAESTHETIC CIRCUITS

CROSS REFERENCE TO RELATED APPLICATION

This application is a continuation-in-part of my copending application, Ser. No. 598,360, filed July 23, 1975, and now abandoned.

FIELD OF THE INVENTION

The present invention relates to a respiratory valve, especially for use in the circuits of anaesthetic gas devices.

BACKGROUND OF THE INVENTION

A known type of respiratory valve has a body member that is tubular and has connected, in axial alignment on opposite sides thereof, two tubular members for inhalation and exhalation, respectively. A conical enlargement of these latter tubular members, at their connecting ends with the body member, provides housings for the mounting and operation of two valve units, for inhalation and exhalation, through a breathing chamber formed in the body member. A tubular mouthpiece member is connected to the body member, perpendicular to the tubular inhalation-exhalation members. The valve units used in this respiratory valve are of a relatively sophisticated structure. They have rigid, flat disks mounted on the end of a short cylindrical tube provided with a fastening flange; the rigid disks are translated and supported by resilient helical strips, so that the gas circulation occurs radially, while by-passing the margins of the disks. This way of operating the valve units presents a relatively large pressure loss and turbulent gas circulation, both in inhalation and in exhalation, that may disturb the patient. On the other hand, the resilient helical strips that operate the translation of the disks in a narrow annular space, may easily lead to the disk being blocked. As a whole, the known valve units are much too sophisticated for their use.

Finally, there are known respiratory and similar devices, having respiratory valves with other structures, in which the connection of the inhalation and exhalation members to the body member presents a V configuration, perpendicular to the tubular mouthpiece member. Such a V shaped connection presents the advantage of a better positioning of the respiratory valve to avoid the destruction of the operating field.

OBJECTS OF THE INVENTION

An object of the present invention is to provide a respiratory valve with a breathing chamber having distinct compartments for the inhalation and exhalation gas, so as to allow a better gas circulation.

Another object of the invention is to provide the respiratory valve body member with a V configuration of the inhalation-exhalation members.

A still further object of the invention is to provide valve units having simple shutters, which ensure a straight-lined laminar gas flow in the two branches, with minimal resistance and without the possibility of blockage.

SUMMARY OF THE INVENTION

Considering these objects, the present invention consists of a respiratory valve, especially for use in the circuits of anaesthetic gas devices and comprises a body-piece having two arms in a V configuration and, at their union, a tubular mouthpiece fitting. One of the arms is intended for inhalation, the other serves for exhalation. To the two arms are connected an inhalation fitting and an exhalation fitting, respectively. Each connection is joint formed with an expanded provided with a seat.

The joint provides a mounting for, and the protection of, a fastening ring, as well as a housing for a shutter, whose resilient membrane closes transversely the passageway of the connected tubular members, while allowing the gas to circulate at a small pressure differential.

BRIEF DESCRIPTION OF THE DRAWING

The above end objects and advantages of the invention will become more apparent from the following drawing, wherein:

FIG. 1 is an exploded longitudinal sectional view of the respiratory valve, with the shutters according to the invention and with the tubular mouthpiece fitting perpendicular to the plane of the V configuration;

FIG. 2 is a cross-sectional view of the respiratory valve of FIG. 1, taken along the line II—II thereof; and FIG. 3 is a sectional view similar to FIG. 1, through another embodiment of the invention.

SPECIFIC DESCRIPTION

The respiratory valve, as shown in FIGS. 1 and 2, comprises a body member 1, with two arms, an inhalation arm $a$ and an exhalation arm $b$, arranged in a V configuration, that forms a bifurcated breathing chamber; the angle of the two arms $a$ and $b$ is an acute one, for instance of 45°. The body member 1 is further provided with a tubular mouthpiece fitting $c_1$, arranged perpendicularly to the plane of the arms in V configuration, $a$ and $b$, connected at the end of their union. At the body-piece 1, the inhalation arm $a$ has the free end enlarged by a tubular portion $a_1$, forming a housing for an inhalation shutter 6, and provided with an inner connecting thread $a_2$.

The exhalation arm $b$ is formed, at the outside, toward its end, with a flange $b_1$, bearing an outer connecting thread $b_5$. At this connection, the sealing occurs by means of a resilient annular packing washer 2. The frontal face of the flange $b_1$ has an annular recessed seat $b_2$, for the fastening ring $g_1$ of an exhalation shutter; the end of the arm $b$ has an annular extension $b_3$, formed with an annular groove $b_4$ to retain the ring of the exhalation shutter.

A tubular inhalation fitting 3 is outwardly provided, toward its connecting end to the arm $a$ with a flange $d_1$, bearing an outer connecting thread $d_5$. The sealing of the connection to the arm $a$ is achieved by means of an annular resilient packing washer 4. The frontal face of the flange $d_1$ has a recessed annular seat $d_2$, for the fastening ring $f_1$ of inhalation shutter 6. The connecting end of the fitting 3 has an annular extension $d_3$ formed with an annular groove $d_4$, to retain the ring of the inhalation shutter 6 by engagement with an inwardly projecting rib $f_3$ formed in ring $f_1$.

The valve further comprises a tubular exhalation fitting 5, that is provided, toward its connecting end to the exhalation arm $b$, with an enlarged tubular portion $e_1$, forming a housing for the exhalation shutter 7, and provided with inner connecting threads $e_2$.

The free ends of the fittings 3 and 5 are provided with circular lugs 3' and 5' for the tight connection of rubber hoses.

The inhalation shutter 6, consisting of a resilient toroidal ring $f_1$, is mounted in the seat $d_2$ from the frontal face of the flange $d_1$ on the tubular inhalation fitting 3, on which ring $f_1$ is fastened by snapping into place on extension $d_3$. Mounted at two diametrically opposed points on the ring $f_1$, is a circular membrane $f_2$, also of resilient material, but thin. The two circular segments of the membrane $f_2$ are very easily bent by the circulation of the inhalation gas. Finally, the valve comprises an exhalation shutter 7, consisting of a resilient toroidal ring $g_1$, mounted in the seat $b_2$ from the frontal face of the flange $b_1$ on the exhalation arm $b$, on which ring $g_1$ is fastened by snapping into place on extension $b_3$. Mounted at opposed points on the ring $g_1$ is a circular membrane $g_2$, also of resilient material, but thin, so that the two circular segments of the membrane are very easily bent, by the circulation of the exhaled gas.

In FIG. 3, the respiratory valve differs from the already described one in that the tubular mouthpiece fitting $c_2$ lies in the same plane as the V configuration formed by the arms $a$ and $b$ of the body member 1.

When used, the tubular mouthpiece fitting $c_1$, or $c_2$ respectively, is connected to the face mask of the patient, while the tubular inhalation fitting 3 and exhalation fitting 5 are connected to the corrugated tubes of the respiratory system not shown in the drawing. At the patient's inhalation, the inhaled gas flow circulates through fitting 3, bends the circular segments of the membrane $f_2$ of the inhalation shutter 4, in the housing of the inhalation arm $a$, as shown in dotted lines in FIG. 1; the low depression that is formed tightens the membrane $g_2$ of the exhalation shutter 7 on the end of the tubular arm $b$. At the patient's exhalation, the low overpressure tightens the membrane $f_2$ of the inhalation shutter 6 on the end of the tubular fitting 3. The evacuated gas thus circulates through the arm $b$, deflecting the circular segments of the membrane $g_2$ of the exhalation shutter 7, in the housing of the exhalation fitting 5, as it is likewise shown in dotted lines in FIG. 1.

The body member 1, arms $a$ and $b$ and fittings 3 and 5 may be made out of any material, preferably of shatter-proof, heat-resistant and transparent plastic. The inhalation shutter 4 and exhalation shutter 2 are made of resilient and heat-resistant material, such as silicone rubber.

It is to be understood that, while there were described certain forms of the invention parts, same is not to be limited to these forms described and shown in the embodiment.

The valve according to the invention present the following advantages:

it ensures a single-sense circulation of the gas in the anaesthetic circuit;
it lowers the resistance in the flow of the inhaled and exhaled gas;
it is simple and uses simple shutters;
it allows a satisfactory running of the anaesthetic circuit, irrespective of its position, without blocking risk.

I claim:

1. A respiratory valve for use in the circuits of anaesthetic gas devices, comprising:
   first and second tubular arms joined in a union with a tubular mouthpiece, said first and second arms forming a bifurcated breathing chamber;
   a first internally threaded enlarged portion formed at the free end of said first arm;
   a first externally threaded flange formed at the free end of said second arm, said flange having an annular recess formed in the end face thereof concentric with an annular extension having a continuous groove in the periphery thereof opening into said recess;
   a first tubular fitting having a second flange identical to said first flange and formed at an end thereof, said second flange being threadedly engaged in said first enlarged portion with sealing means therebetween;
   a first shutter having a resilient toroidal ring formed with an inwardly projecting rib, said ring being removably mounted in said annular recess in said second flange with said rib engaged in said groove and a resilient circular membrane overlying said ring and mounted thereon at two diametrically opposite points defining two deflectable circular segments, said first shutter being housed in said first enlarged portion in an inhalation mode;
   a second tubular fitting having a second enlarged portion formed at an end thereof and identical to said first enlarged portion, said second enlarged portion being threadedly engaged on said first flange with sealing means therebetween
   a second shutter identical to said first shutter, mounted in said annular recess of said first flange in an identical manner to the mounting of said first shutter, said second shutter being housed in said second enlarged portion in an exhalation mode; and
   circular lugs formed on the outer periphery of said first and second fittings for engagement with said circuit.

2. The respiratory valve as defined in claim 1 wherein said first and second arms are arranged in a V configuration.

3. The respiratory valve as defined in claim 2 wherein said mouthpiece joins said first and second arms perpendicular to the plane of said V configuration.

4. The respiratory valve as defined in claim 2 wherein said mouthpiece lies in the same plane with said V configuration.

* * * * *